(12) United States Patent
Pütter et al.

(10) Patent No.: US 7,220,242 B2
(45) Date of Patent: May 22, 2007

(54) WITHDRAWAL DEVICE FOR THE SECURE WITHDRAWAL OF A FLEXIBLE PUNCTURE NEEDLE FROM A CATHETER, IN PARTICULAR FROM A CATHETER WITH A FLEXIBLE CATHETER TUBE

(75) Inventors: Harry Pütter, Bad Salzschlirf (DE); Jörg Heinzerling, Bad Hersfeld (DE)

(73) Assignee: Clinico GmbH, Bad Hersfeld (DE)

( * ) Notice: Subject to any disclaimer, the term of this patent is extended or adjusted under 35 U.S.C. 154(b) by 0 days.

(21) Appl. No.: 11/262,046

(22) Filed: Oct. 28, 2005

(65) Prior Publication Data
US 2006/0106335 A1    May 18, 2006

(30) Foreign Application Priority Data
Nov. 17, 2004    (DE)    ................ 20 2004 017 861 U

(51) Int. Cl.
*A61M 31/00*    (2006.01)
(52) U.S. Cl. .................................. 604/93.01
(58) Field of Classification Search ................ 604/263, 604/192, 93.01, 164.08, 110, 158
See application file for complete search history.

(56) References Cited

U.S. PATENT DOCUMENTS

| 4,950,252 | A | * | 8/1990 | Luther et al. ................ 604/198 |
| 5,476,106 | A | | 12/1995 | Gartz |
| 6,056,718 | A | | 5/2000 | Funderburk et al. |
| 6,942,642 | B2 | * | 9/2005 | Suzuki ........................ 604/110 |
| 2004/0158207 | A1 | | 8/2004 | Hunn et al. |

FOREIGN PATENT DOCUMENTS

| EP | 1331018 | 7/2003 |
| WO | WO 02/100263 | 12/2002 |

* cited by examiner

*Primary Examiner*—Nicholas D. Lucchesi
*Assistant Examiner*—Christopher D. Koharski
(74) *Attorney, Agent, or Firm*—Friedrich Kueffner

(57) ABSTRACT

A withdrawal device for the secure withdrawal of a puncture needle from a catheter, in particular from a catheter with a flexible catheter tube following the puncture. The device including a connection section for connecting the withdrawal device with the catheter in a starting position of use and a return-motion lever linearly movable in the guide element, whereby linear toothing is affixed to one of the elements, guide element and return-motion lever, which meshes with the peripheral toothing of a pivoted gearwheel on the other element (return-motion lever, guide element), and whereby the puncture needle is attached with the end protruding from the catheter such that upon rotation of the gearwheel, the puncture needle is wound up on a takeup part fixedly attached thereto.

10 Claims, 5 Drawing Sheets

WITHDRAWAL DEVICE FOR THE SECURE WITHDRAWAL OF A FLEXIBLE PUNCTURE NEEDLE FROM A CATHETER, IN PARTICULAR FROM A CATHETER WITH A FLEXIBLE CATHETER TUBE

BACKGROUND OF THE INVENTION

1. Field of the Invention

The present invention relates to a withdrawal device for the secure withdrawal of a puncture needle from a catheter, in particular from a catheter with a flexible catheter tube.

2. Description of the Related Art

In medicine, catheters are used in various fields for administering drugs which have been dissolved or suspended in fluid. Using catheters medication can be directly administered into the patient's tissue or bloodstream via a puncture site. In order to attach the catheter it is necessary to create an entry into the tissue or bloodstream of the patient by means of a puncture. Various puncture configurations are known for this purpose.

Puncture configurations of the type initially described are especially intended for independent use by the patient, for example, for administering insulin with the aid of an insulin pump.

For puncture configurations featuring a flexible catheter tube and a puncture needle, when the catheter hub is attached to the skin surface of the patient, the underlying tissue is pierced by the puncture needle, while the flexible catheter tube is inserted into the tissue in the process. The patient's stomach area is frequently chosen as the incision site for the puncture configuration. Following insertion, the puncture needle must be withdrawn and removed, so that only the catheter tube remains in the puncture site. The catheter hub is then hooked up to an infusion line and therefore, to medication delivery. On the one hand, the withdrawal of the puncture needle should be effected quickly and safely. On the other, the puncture needle should if possible be encapsulated after withdrawal but at the very least protected against open exposure. This serves to reduce and if possible completely rule out the danger of injury by means of a needle contaminated with bodily fluid and the danger of infection associated therewith.

SUMMARY OF THE INVENTION

The withdrawal device according to the invention meets these requirements.

According to the present invention, a withdrawal device is proposed for the secure withdrawal of a flexible puncture needle from a catheter, in particular a catheter with a flexible tube after puncturing and characterized by a connection section for connecting the withdrawal device with the catheter in a starting position of use and a return-motion lever linearly movable in the guide element, whereby linear toothing is affixed to one of the elements, guide element and return-motion lever, which meshes with the peripheral toothing of a pivoted gearwheel on the other element (return-motion lever, guide element), and whereby the puncture needle is attached with the end protruding from the catheter such that upon rotation of the gearwheel, the puncture needle is wound up on a takeup part fixedly attached thereto.

The gist of the withdrawal device according to the present invention resides in that a simplified "gearing" mechanism is used to withdraw the puncture needle from the catheter. The back end of the puncture needle is attached to the gearwheel such that when the return-motion lever is pulled back, the peripheral teeth of gearwheel act together with the linear toothing to initiate the rotation of the gearwheel. The puncture needle is thereby taken up onto the reeling section of the gearwheel. In this manner, the puncture needle together with its sharp end is withdrawn from the catheter and pulled into the withdrawal device.

In the starting position of use the withdrawal device comprising a guide element and return-motion lever is connected at its connection section with the corresponding complementary-shaped connection section of the catheter. The unit comprising the withdrawal device and catheter is delivered in this starting position of use such that a user can apply the catheter. After inserting the catheter, the user withdraws the puncture needle from the catheter by pulling back the return-motion lever and then detaches the withdrawal device from the catheter. The catheter is then ready to be hooked up to an infusion line.

The linear teeth are preferably arranged on the guide element and the gearwheel is pivoted on a tappet securely fastened to the return-motion lever. This configuration has the advantage that when pulling back the return-motion lever the withdrawal of the needle from the catheter is not only effected by the reeling of the back puncture needle end, but also by the linear movement of the gearwheel with the return-motion lever. In this manner the withdrawal effect is doubled, making an overall compact design of the withdrawal device possible. In order to generate the force necessary to withdraw the puncture needle from the catheter without requiring an excessive force when pulling back the return-motion lever and in order to keep the required path of the return-motion lever as short as possible, it is practical to dimension the linear toothing and the peripheral toothing such that a suitable gearing-up or gearing-down results for the mentioned objectives.

A withdrawal device encompassing further advantageous embodiments according to the invention provides a secure protection for the tip of the puncture needle after withdrawal, so that accidental injuries caused by improper handling of the puncture needle and infection dangers associated therewith can be prevented.

In order to simplify the movement (normally pulling back) of the return-motion lever, a grip section is provided in an advantageous further embodiment of the present invention. The guide element may also be equipped with a grip section as a thrust bearing, so that the return-motion lever can be operated with one hand and the puncture needle is thereby withdrawn from the catheter.

As a further advantageous embodiment of the present invention locking means are provided. The locking means lock the return-motion lever at least in its end position after the withdrawal of the puncture needle. However, the locking means can also additionally secure the return-motion lever in its starting position of use. The locking means that lock the return-motion lever in the position first mentioned provide the advantage that the puncture needle once withdrawn from the catheter cannot accidentally be exposed again at its sharp end after withdrawal. This requires that the return-motion lever is locked in its end position. By locking the return-motion lever in the starting position of use, it is possible to prevent accidental movement of the return-motion lever and the premature withdrawal of the puncture needle from the catheter while inserting the catheter.

In a further advantageous embodiment of the present invention it is ensured that the withdrawal device cannot be prematurely detached from the catheter. This guarantees that the withdrawal device can only be separated from the catheter once the puncture needle has been completely withdrawn from the catheter. This also prevents a premature and unintentional withdrawal of the puncture needle from the catheter or a detaching of the withdrawal device while the puncture needle is still inside the catheter.

The withdrawal device according to the invention can be manufactured relatively easily if the individual parts are made of plastic and preferably injected molded.

A handle on the withdrawal device presents a further advantageous embodiment of the invention that simplifies the removal of the withdrawal device from the catheter once the puncture needle has been withdrawn therefrom.

The various features of novelty which characterize the invention are pointed out with particularity in the claims annexed to and forming a part of the disclosure. For a better understanding of the invention, its operating advantages, specific objects attained by its use, reference should be had to the drawing and descriptive matter in which there are illustrated and described preferred embodiments of the invention.

DETAILED DESCRIPTION OF THE INVENTION

Figure 1:
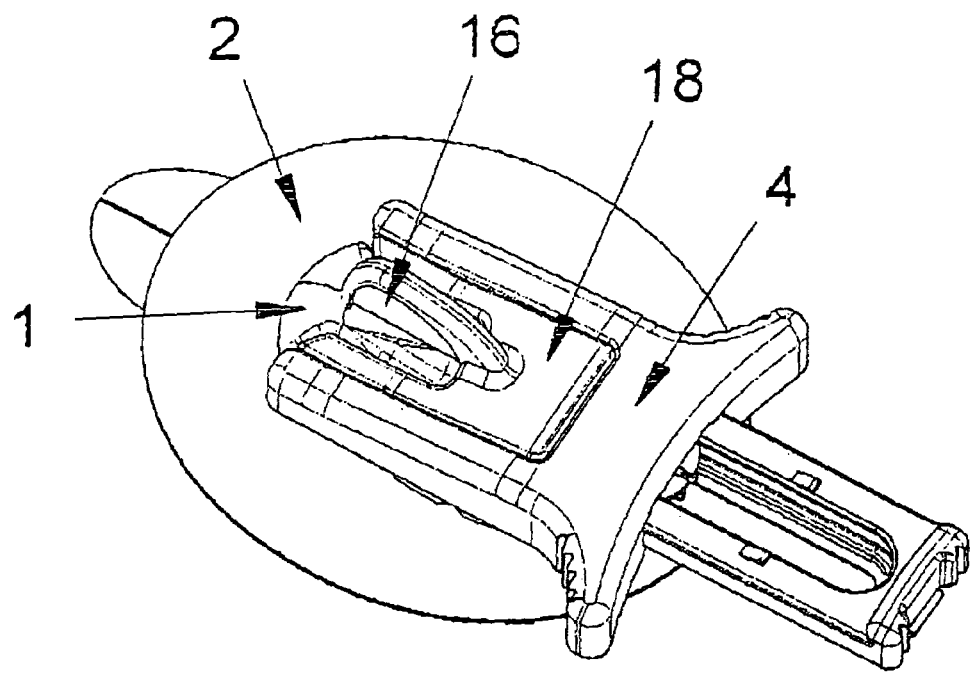
FIG. 1 is a perspective view of a withdrawal device according to the present invention connected with a catheter.

The withdrawal device according to the invention is referred to as needle draw unit 18 in the figures. The needle draw unit 18 is basically comprised of an elongated guide element 11 and a return-motion lever 4 guided linearly in the guide element 11.

The needle draw unit 18 is intended to be connected with a catheter 1. The catheter 1 in this example is a catheter with a flexible catheter tube 24. The catheter 1 is mounted on an adhesive plate 2 which can be secured on the skin surface of the patient.

Figure 2:
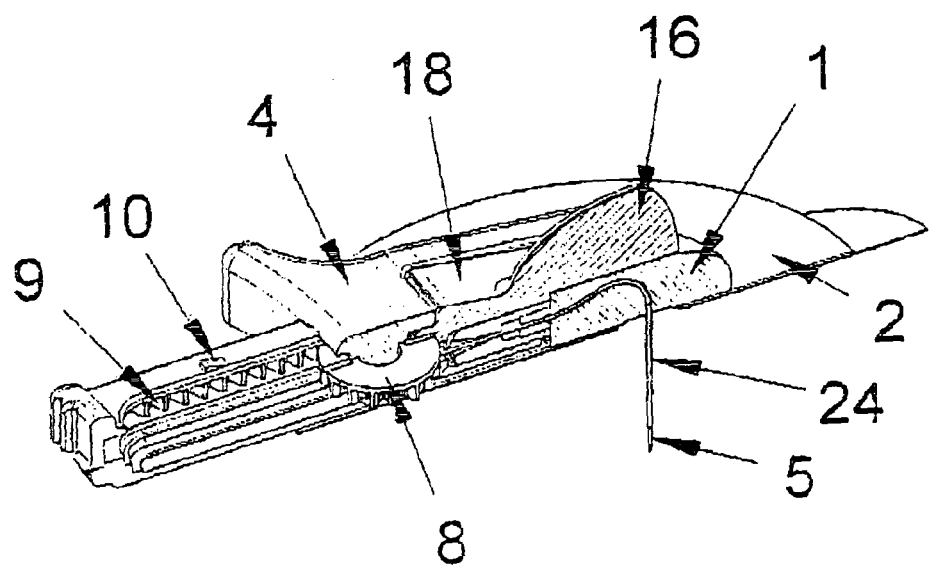
FIG. 2 is a sectional view of the arrangement combination from FIG. 1, cut along the longitudinal mid-perpendicular axis.
Figure 3:
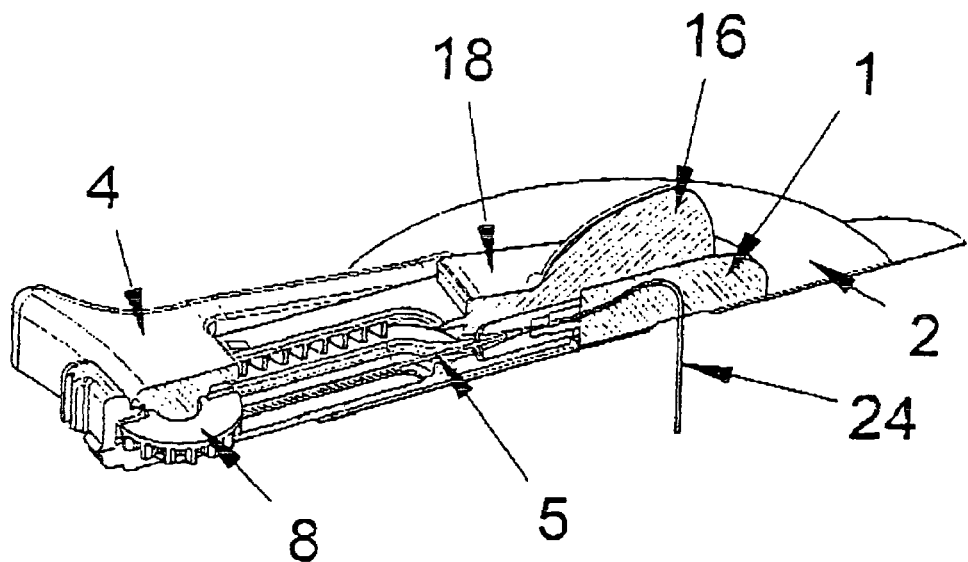
FIG. 3 is a sectional view corresponding to FIG. 2 with a return-motion lever of the withdrawal device shown pulled back in a rear position.
Figure 4:
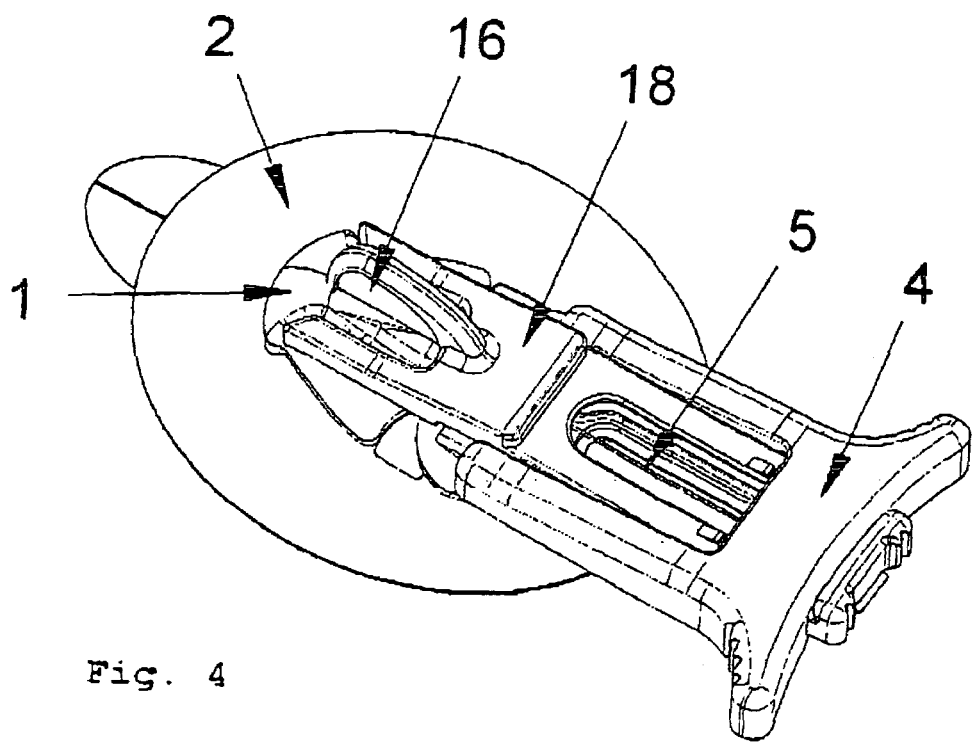
FIG. 4 is a foreshortened view corresponding to FIG. 1 with a return-motion lever of the withdrawal device shown pulled back in a rear position.
Figure 5:
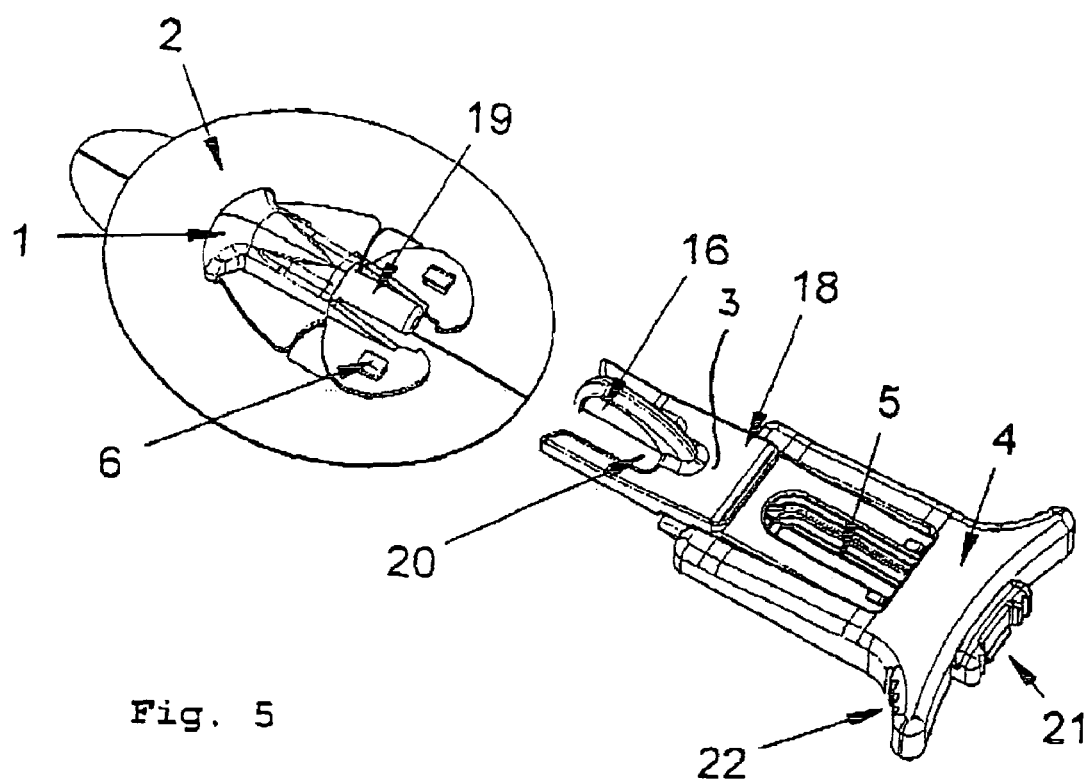
FIG. 5 shows a catheter and a withdrawal device detached from one another.

In an initial starting position of use shown in FIGS. 1 and 2, the needle draw unit 18 is connected with the catheter 1.

Figure 6:
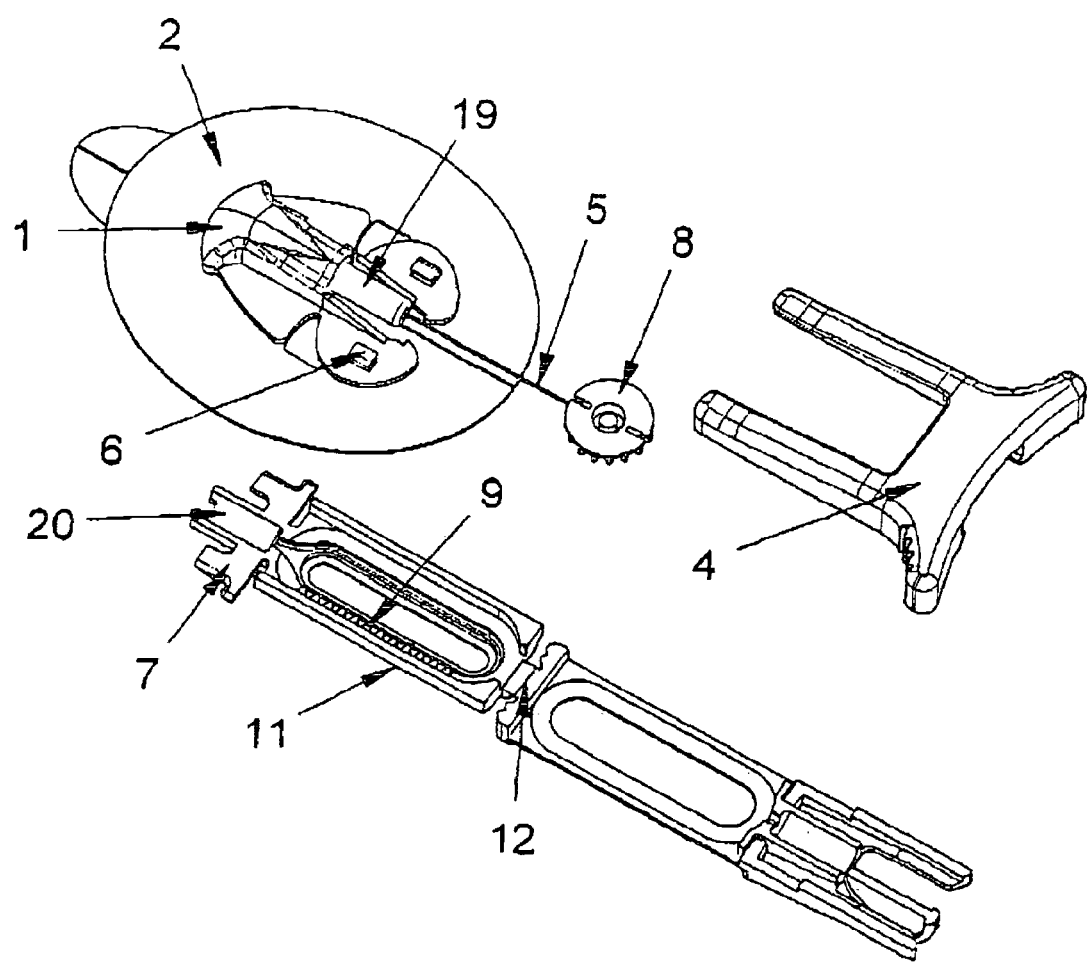
FIG. 6 shows a blown-up view of the catheter and the withdrawal device including all individual parts.
Figure 7:
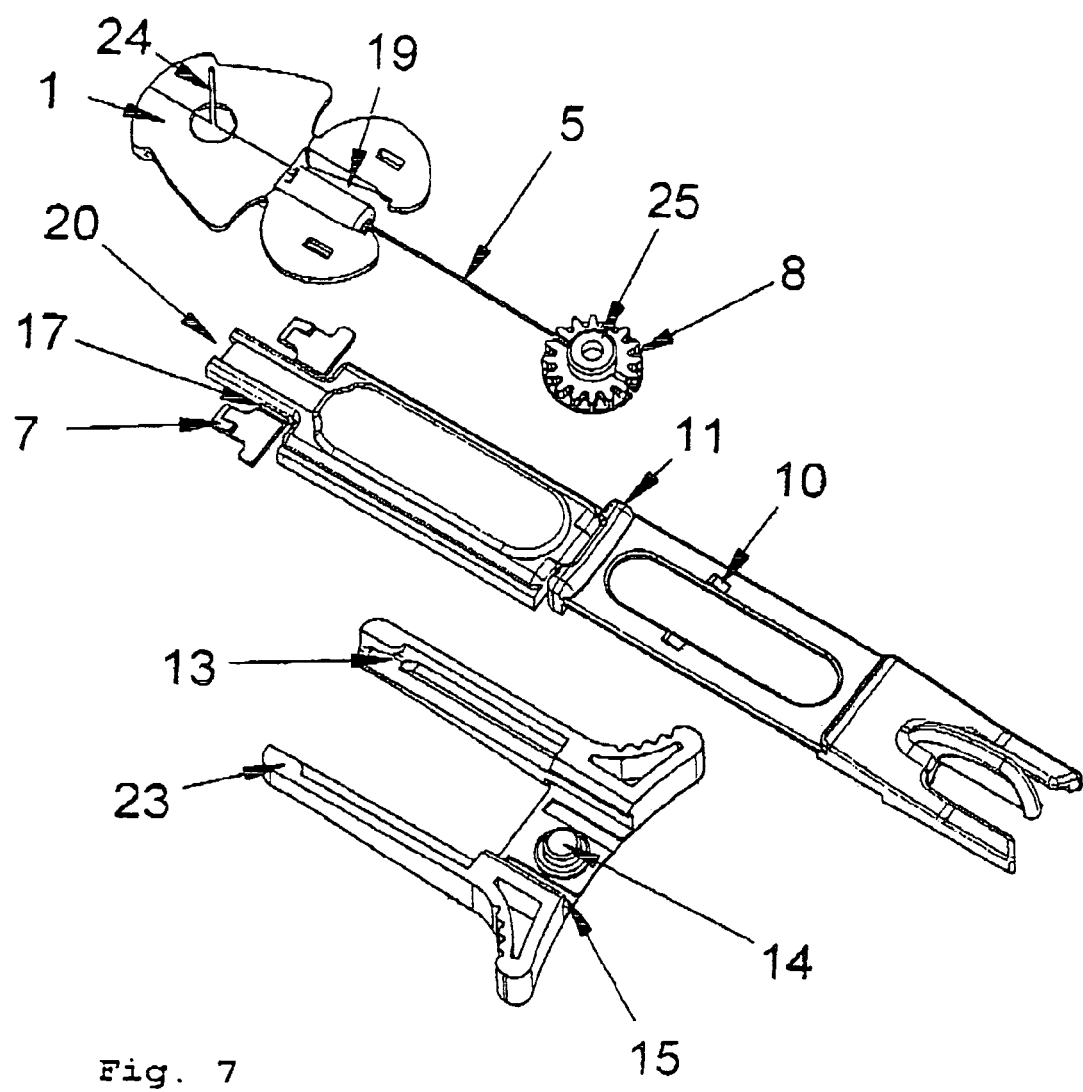
FIG. 7 is similar to FIG. 6 showing the elements from a bottom view.

FIGS. 6 and 7 provide a particularly good illustration of the needle draw unit 18 and its exact design. The guide element 11 is built like a housing which features linear toothing in the form of a toothed rack 9 on a side wall. For reasons of uncomplicated production and assembly the guide element 11 is injection-molded out of plastic material and comprises a one-piece bottom part in which the toothed rack 9 is arranged, and a cover, wherein both elements, the bottom part and the cover, are connected by means of a film hinge 12. A gearwheel 8 is placed in the guide element 11 such that the peripheral toothing of the gearwheel 8 meshes with the linear toothing of the toothed rack 9. The gearwheel 8 exhibits a securely fixed takeup shaft 25, wherein the back end of puncture needle 5 extending into the catheter 1 and through the flexible catheter tube 24 is fastened at the takeup shaft 25. When the needle draw unit 18 is assembled, the gearwheel 8 is pivoted on a tappet 14 which is securely fastened with the return-motion lever 4. The return-motion lever 4 engages the guide element with overarms 23 or with fastening hooks 15 in the form of undercuts, so that it can be moved linearly in a steered motion in the guide element 11. The guide element 11 exhibits at its front end a connection section 20 for connecting with a complementary shaped connection section 19 on the catheter 1. The connection section 19 on the catheter 1 is a circular, cylindrically shaped tappet, while the connection section 20 on the needle draw unit 18 correspondingly is a complementary shaped bush. The puncture needle 5 extends through a passage in the connection section 19 of the catheter 1, i.e., through the circular, cylindrically shaped tappet, into the flexible catheter tube 24 and out through the front end thereof.

Two hooks 7 are also arranged on the guide element 11 at the front thereof with the connection section 20 which are connected via foil joints 17 with the connection section 20 in one piece.

Webs 10 are built in the cover piece of the guide element 11.

There are guiding ways 13 on the return-motion lever 4 in the front sections of the overarms 23 which are inclined in the longitudinal direction of the overarms 23. The return-motion lever 4 also has a gripping piece 22. Another gripping piece 21 is located at the back end of the guide element 11, i.e., opposite the connection section 20 thereof. The guide element 11 exhibits a handle 16 firmly connected to the guide element in the area of the connection section 20.

Finally, the catheter has hook-shaped rear grips 6.

The needle draw unit 18 according to the invention and described in the figures works as follows:

In the starting position (FIG. 1 and FIG. 2) the return-motion lever 4 is situated fully shifted toward the end of the guide element 11 with the connection section 20 in starting position of use. In this way the gearwheel 8 is closest to the opening in the connection piece 19 of the catheter and is fixedly connected to the rear end of the puncture needle 5. The flexible puncture needle 5 extends the length of the catheter and out through the open end of the catheter tube 24. The needle draw unit 18 is connected with the catheter 1 by means of the interaction between the connection section 19 of the catheter 1 and the connection section 20 of the needle draw unit 18, whereby the interaction of the hooks 7 on the needle draw unit 18 and the rear grips 6 on the catheter 1 affect a locking of the elements needle draw unit 18 and the catheter 1.

In this position either the patient applies or the catheter is applied to the patient, whereby the unit comprising needle draw unit 18 and the catheter 1 is held by the handle 16 of the needle draw unit 18 and the puncture needle 5 with the flexible catheter tube 24 is inserted into the tissue. The catheter 1 is then attached to the skin of the patient by means of the adhesive disk 2. Now the puncture needle 5 can be withdrawn from the flexible catheter tube 24 and the catheter 1. The return-motion lever is thereby grasped preferably at the gripping pieces 22, ideally with the index finger and the middle finder of one hand, and pulled with backpressure, usually with the help of the thumb at the gripping piece 21 of the guide element 11 from its front starting position of use to a back end position. When passing over the webs 10 there is a noticeable and audible signal indicating to the user that the return motion lever is securely in its end position. The return-motion lever 4 is simultaneously locked in its end position.

When pulling back the return-motion lever 4, the gearwheel 8 is simultaneously pulled back by means of the tappet 14 and the meshing of its peripheral teeth with the toothed rack 9 actuates the rotation of the gearwheel. During rotation the rear end of the flexible puncture needle 5 is wound up onto the takeup shaft 25 on the gearwheel 8 and thereby withdrawn from the catheter 1 and the flexible catheter tube 24. An additional traction force arises from the overall linear backwards motion of the return-motion lever, so that a withdrawal of the puncture needle 5 from the catheter 1 is affected by combination of backwards movement of the return-motion lever 4 and the rotation of the gear wheel 8.

While pulling back the return-motion lever 4 into the end position the guiding ways pass the hooks clasping at the lateral extensions thereof. Due to the inclined form of the guiding ways the hooks 7 are then lifted, whereby they are moved around the foil joints 17. The hooks 7 are thereby separated from the rear grips 6. Thus, by pulling on the handle 16 the needle draw unit can be detached from the catheter 1 and disposed of.

The relationship between the teeth of the toothed rack 9 and the peripheral toothing of the gearwheel 8 is chosen such that, on the one hand the force needed for withdrawing the puncture needle 5 from the catheter 1 can be mustered with a normal force applied to the return-motion lever while pulling it back into its end position, and on the other hand, the longitudinal extension of the guide element 11 is kept as short as possible so that the overall size of the needle draw unit 18 is as small as possible.

The needle draw unit 18 is designed and dimensioned such after the puncture needle 5 is withdrawn from the catheter 1, i.e., when the return-motion lever 4 is in its end position, the tip of the puncture needle 5 is located in the interior of the connection section 20 formed in guide element 11 and thus under a covering 3. In this way it is certain that the tip of the puncture needle S is not exposed after withdrawal and injuries and infections connected therewith are prevented.

The assembly of the needle draw unit 18, or the unit comprising the needle draw unit 18 and the catheter 1 respectively, is as follows:

First, the gearwheel 8 is attached to the end of the puncture needle 5 which extends out of the catheter 1, or a puncture needle 5 which is already attached to a gearwheel 8 is inserted into a catheter 1. Then the guide element 11 is placed in an open position (see FIG. 6 and FIG. 7) with its connection section 20 over the connection piece 19 of the catheter 1 and the gearwheel 8 is placed in the housing in the lower part of the guide element 11, whereby the peripheral teeth of the gearwheel are meshed with the teeth of the toothed rack.

The guide element is closed by turning the cover down along the film hinges 12, thereby fixing the connection section 20 to the connection section 19 of the catheter 1. Locking devices which are not shown herein warrant a secure and tight connection of both housing and cover parts of the guide element 11. Finally, the return-motion lever 4 is fit into the guide element 11 such that the tappet 14 clasps the gearwheel 6 and that the overarms 23 and the fastening hooks 15 with the guide element 11 can together effect the direction of the return-motion lever 4. The return-motion lever 4 is fastened to the guide element 11 by means of the fastening hooks 15.

The unit comprising the catheter 1 and the needle draw unit 18 is now ready in its starting position of use and can be deployed by the patient.

While specific embodiments of the invention have been shown and described in detail to illustrate the inventive principles, it will be understood that the invention may be embodied otherwise without departing from such principles.

We claim:

1. A withdrawal device for the secure withdrawal of a flexible puncture needle from a catheter, in particular from a catheter with a flexible catheter tube following the puncture, the withdrawal device comprising
a connection section for connecting the withdrawal device with the catheter in a starting position of use, and
a return-motion lever linearly movable in a guide element, wherein a linear toothing is affixed to one of the guide element and the return-motion lever, wherein the linear toothing meshes with a peripheral toothing of a pivoted gearwheel on another of the return-motion lever, and the guide element, and wherein the puncture needle is attached with the end protruding from the catheter such that upon rotation of the gearwheel, the flexible puncture needle is wound up on a takeup part fixedly attached to the gearwheel.

2. The withdrawal device according to claim 1, wherein the linear toothing is arranged on the guide element and the gearwheel is arranged on the return-motion lever, wherein the gearwheel is pivoted on a tappet which is securely fastened to the return-motion lever.

3. The withdrawal device according to claim 1, wherein the linear toothing and the peripheral toothing of the gearwheel are chosen so as to set a pre-selected gearing-up or gearing-down.

4. The withdrawal device according to claim 1, wherein the guide element has a cover for securely taking in the tip of the puncture needle at least in an area where the tip of the puncture needle is located after its withdrawal from the catheter.

5. The withdrawal device according to claim 1, wherein the return-motion lever has a gripping piece for gripping when moving back the return-motion lever.

6. The withdrawal device according to claim 1, wherein locking devices are provided for securing the return-motion lever relative to th& guide element at least in the position assumed after withdrawing the puncture needle.

7. The withdrawal device according to claim 1, wherein locking devices are provided for locking the connection section with a corresponding counterpart of the catheter, and devices provided for disconnecting the locking devices in order to detach the withdrawal device from the catheter, wherein the devices for disconnecting the locking devices are connected with the return-motion lever in such a way that the locking devices only disconnect once the return-motion lever has reached its end position furthest away from the catheter.

8. The withdrawal device according to claim 1, wherein at least the return-motion lever and the guide element are made of plastic.

9. The withdrawal device according to claim 1, wherein at least the return-motion lever and the guide element are injection molded.

10. The withdrawal device according to claim 1, further comprising a handle for detaching the withdrawal device from the catheter.

* * * * *